(12) United States Patent
Ponce et al.

(10) Patent No.: US 10,206,728 B2
(45) Date of Patent: Feb. 19, 2019

(54) FIXATION DEVICE FOR PROXIMAL HUMERUS FRACTURES

(71) Applicant: Wright Medical Technology, Inc., Memphis, TN (US)

(72) Inventors: Brent A. Ponce, Homewood, AL (US); John Whitcomb, Birmingham, AL (US)

(73) Assignee: Wright Medical Technology, Inc., Memphis, TN (US)

( * ) Notice: Subject to any disclaimer, the term of this patent is extended or adjusted under 35 U.S.C. 154(b) by 565 days.

(21) Appl. No.: 14/796,251

(22) Filed: Jul. 10, 2015

(65) Prior Publication Data

US 2015/0313653 A1 Nov. 5, 2015

Related U.S. Application Data

(63) Continuation-in-part of application No. PCT/US2014/011113, filed on Jan. 10, 2014.

(Continued)

(51) Int. Cl.
*A61B 17/80* (2006.01)
*A61B 17/17* (2006.01)
*A61B 17/88* (2006.01)

(52) U.S. Cl.
CPC ...... *A61B 17/8061* (2013.01); *A61B 17/1739* (2013.01); *A61B 17/809* (2013.01);
(Continued)

(58) Field of Classification Search
CPC . A61B 17/7059; A61B 17/80; A61B 17/8052; A61B 17/8057; A61B 17/8061; A61B 17/842
See application file for complete search history.

(56) References Cited

U.S. PATENT DOCUMENTS 7,655,029 B2 * 2/2010 Niederberger ..... A61B 17/8061
606/280
7,927,333 B2 4/2011 Gradl
(Continued)

FOREIGN PATENT DOCUMENTS

CN 201920886 U 8/2011
CN 102835998 A 12/2012
(Continued)

OTHER PUBLICATIONS

Patent Examination Report No. 2 issued for corresponding Australian patent application No. 2014205267, dated Feb. 15, 2017, 6 pages.
(Continued)

*Primary Examiner* — Anu Ramana
(74) *Attorney, Agent, or Firm* — Duane Morris LLP

(57) ABSTRACT

A fixation device is disclosed for the fixation of proximal humerus fractures includes an implantable humerus plate having a proximal portion adapted to be positioned at a head and medial calcar of the humerus, a distal portion adapted to be positioned along a shaft of the humerus, and a plurality of calcar openings provided through the proximal portion adapted to receive calcar fasteners that extend into the medial calcar. The calcar fasteners are grouped into a rafted configuration and the tips of each fastener are positioned into the calcar region so that torsional forces bearing upon the calcar regions are distributed into the rafted fastener support, thereby avoiding varus collapse of the humerus head after fixation of the fracture.

20 Claims, 6 Drawing Sheets

Related U.S. Application Data

(60) Provisional application No. 61/751,485, filed on Jan. 11, 2013.

(52) U.S. Cl.
CPC ...... *A61B 17/8019* (2013.01); *A61B 17/8042* (2013.01); *A61B 17/8866* (2013.01); *A61B 17/1778* (2016.11)

(56) References Cited

U.S. PATENT DOCUMENTS

| | | |
|---|---|---|
| 2004/0225291 A1 | 11/2004 | Schwammberger et al. |
| 2005/0165395 A1 | 7/2005 | Orbay et al. |
| 2006/0264956 A1 | 11/2006 | Orbay et al. |
| 2008/0188852 A1 | 8/2008 | Matityahu |
| 2009/0069851 A1 | 3/2009 | Gillard et al. |
| 2010/0076436 A1 | 3/2010 | Hajianpour |
| 2010/0324602 A1 | 12/2010 | Huebner et al. |
| 2011/0224736 A1 | 9/2011 | Humphreys |
| 2012/0179208 A1 | 7/2012 | Geissler et al. |
| 2013/0096629 A1* | 4/2013 | Rollinghoff ............ A61B 17/80 606/281 |
| 2014/0128921 A1* | 5/2014 | Parsons .............. A61B 17/8061 606/281 |

FOREIGN PATENT DOCUMENTS

| | | |
|---|---|---|
| EP | 2474278 A2 | 7/2012 |
| WO | 2012/058448 A2 | 5/2012 |

OTHER PUBLICATIONS

Second Office Action issued for Chinese patent application No. 201480005139.3, dated Jun. 20, 2017, 17 pages.

International Search Report and Written Opinion issued for corresponding International patent application No. PCT/US2014/011113, dated Apr. 7, 2014, 17 pages.

Patent Examination Report No. 1 issued for corresponding Australian patent application No. 2014205267, dated Feb. 23, 2016, 3 pages.

First Office Action issued for corresponding Chinese patent application No. 201480005139.3, dated Oct. 24, 2016, 16 pages.

Office Action issued in connection with Canadian patent application No. 2,897,974, dated Dec. 19, 2017, 4 pages.

Third Office Action issued in connection with Chinese patent application No. 201480005139.3, dated Jan. 3, 2018, 8 pages.

Office Action issued in connection with Canadian Patent Application No. 2,897,974, dated Oct. 4, 2018, 5 pages.

* cited by examiner

FIXATION DEVICE FOR PROXIMAL HUMERUS FRACTURES

This application claims the benefit of filing priority under 35 U.S.C. § 119 and 37 C.F.R. § 1.78 of PCT Application Serial No. PCT/US2014/011113 filed Jan. 10, 2014, for an APPARATUS FOR THE FIXATION OF PROXIMAL HUMERUS FRACTURES which in turn claims priority to U.S. Provisional Application Ser. No. 61/751,485, filed Jan. 11, 2013, for a CALCAR OSTEOSYNTHESIS FOR PROXIMAL HUMERUS FRACTURES. All information disclosed in those prior applications are incorporated herein by reference

FIELD OF THE INVENTION

The present invention relates generally to surgical plates for the mending of broken bones in the human body. In particular, the present invention relates to fixation plates for the upper arm or humerus. In even further detail, the present invention relates to fixation plate strategies to avoid varus collapse of the humerus head.

BACKGROUND OF THE INVENTION

When a proximal humerus fracture occurs, it is sometimes necessary to fix the bone fragments together to ensure proper healing and restore correct function of the arm and shoulder. Such fixation can be achieved by securing a plate to the lateral side of the humerus adjacent the head of the humerus using screws or pins.

While such procedures can be effective, it is not uncommon for varus collapse 15 to occur in which the head of the humerus collapses and forms an undesirably acute angle (e.g., 80 to 90°) with the neck of the humerus. It is important to prevent such collapse because it can alter the biomechanics of the shoulder joint, decrease range of motion, and lead to unsuccessful outcomes. In view of the above discussion, it can be appreciated that it would be desirable to have apparatus that enables fixation of proximal humerus fractures but prevents varus collapse.

SUMMARY OF THE INVENTION

The herein described fixation device allows for fixation of proximal humerus fractures and prevents varus collapse of the humerus during rehabilitation. Generally, the apparatus includes a humerus plate that that includes two groups of apertures in the proximal portion of the fixation device. One group receives fasteners to secure an upper portion of the plate to the humeral head and another group receives fasteners that transcend the surgical neck and lateral inferior portion of said humeral head and penetrate the calcar region of the humerus. The fasteners are sized so that their tips extend into the cortical portion of said calcar proximal the medial concave portion of said calcar, and said tips are arranged so that they define an arc substantially congruent with an arc defined by the exterior surface of said medial concave portion of the calcar. The calcar fasteners may have varying angles to enhance columnated support within the humerus, such angles creating intersecting fastener positions. Further fasteners are threaded into the shaft of the humerus through the distal portion of the plate from the lateral side of the bone to provide further reinforcement.

Other features and objects and advantages of the present invention will become apparent from a reading of the following description as well as a study of the appended drawings.

BRIEF DESCRIPTION OF THE DRAWINGS

A fixation device incorporating the features of the invention is depicted in the attached drawings which form a portion of the disclosure and wherein.

DESCRIPTION OF THE PREFERRED EMBODIMENTS

In the following disclosure, various specific embodiments are described. It is to be understood that those embodiments are example implementations of the disclosed inventions and that alternative embodiments are possible. All such embodiments are intended to fall within the scope of this disclosure.

Figure 1:
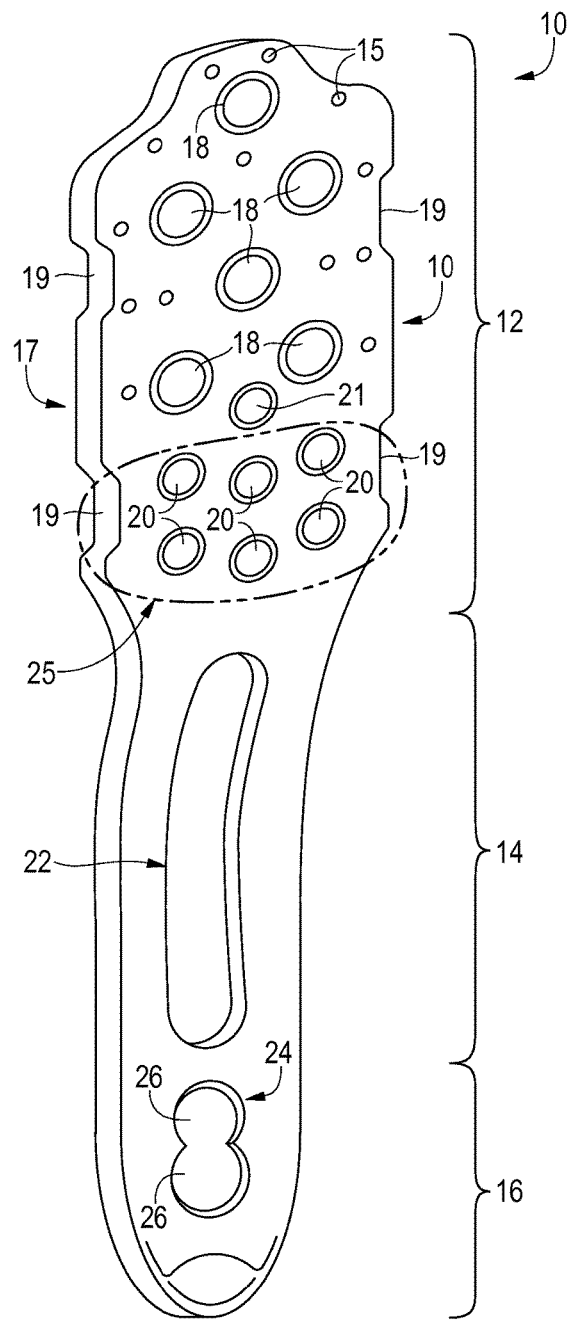
FIG. 1 is a perspective view of an embodiment of a humerus plate that can be used to fix a proximal humerus fracture.
Figure 2:
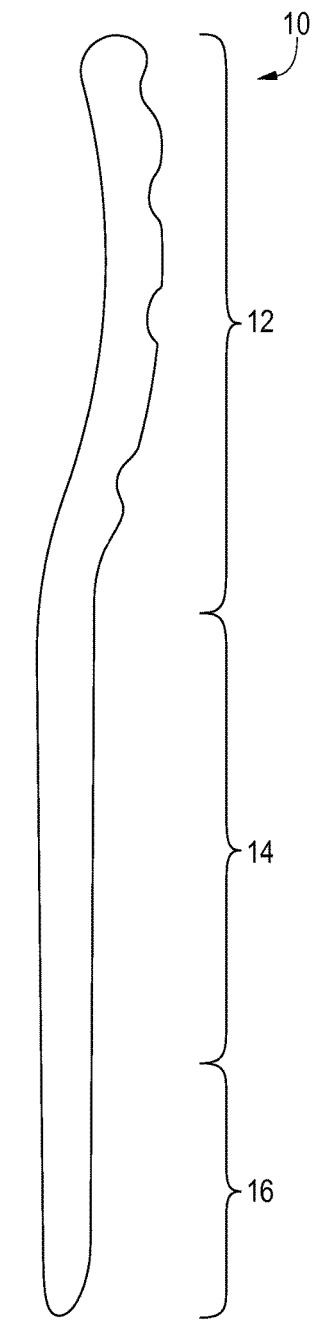
FIG. 2 is a side view of the humerus plate of FIG. 1.

FIGS. 1 and 2 illustrate an embodiment of an implantable humerus plate 10 that can be used to secure bone fragments of the proximal humerus together. As shown in the figures, the illustrated humerus plate 10 is unitarily formed from a single piece of material, such as stainless steel or titanium. The humerus plate 10 is generally flat, narrow, and elongated so as to be well suited for attachment to the lateral portion of the head, neck, and shaft of the humerus bone. As is illustrated most clearly in FIG. 2, however, the proximal portion 12 of the humerus plate 10 has a gentle curvature that is adapted to match the convex curvature of the head of the humerus bone (see FIG. 4). As is further shown in FIG. 2, however, the central portion 14 and the distal portion 16 of the humerus plate 10 can be generally linear (when viewed from the side). In some embodiments, the humerus plate 10 is approximately 80 to 100 mm long and approximately 2 to 5 mm thick, but will vary to suit a particular patient anatomy as may be known in the art.

With particular reference to FIG. 1, the proximal portion 12 of the humerus plate 10 is wider than the central and distal portions 14, 16 of the plate. In some embodiments, the proximal portion 12 is approximately 18 to 20 mm wide and the central and distal portions 14, 16 are approximately 10 to 14 mm wide. As is further shown in FIG. 1, the proximal portion 12 can have a generally rectangular shape that is defined in part by generally linear lateral edges 17. In some embodiments, the lateral edges 17 include notches 19 that, as described below, facilitate attachment of another device to the humerus plate 10 during the fixation procedure. Each of the herein included embodiments includes suture holes 15 around the upper periphery of the plate 10.

With further reference to FIG. 1, each of the portions 12-16 of the humerus plate 10 comprises its own opening or openings. Beginning with the proximal portion 12, there are multiple relatively large openings 18 provided in the upper part of the proximal portion and multiple relatively small openings 20 provided in the lower part of the proximal portion. In some embodiments, the relatively large openings 18 are approximately 3 to 5 mm in diameter and the relatively small openings 20 are approximately 2 to 3 mm in diameter. In the illustrated example, there are six relatively large openings 18 that are generally equidistantly spaced from each other and six relatively small openings 20 that are arranged to two generally parallel rows of three openings each. Notably, greater or fewer numbers of openings and different positioning of the openings can be used depending upon the nature of the fixation that is to be performed. As described below, the relatively large openings 18 are adapted to receive fasteners that will extend into the proximal head of the humerus bone and the relatively small openings 20 are adapted to receive fasteners that will extend into the medial calcar of the humerus bone. In view of this, the relatively large openings 18 may be referred to as proximal openings and the relatively small openings 20 may be referred to as calcar openings. In addition, the calcar openings can be considered as being located in a calcar region of the humerus plate, which is located at a position approximately one-fourth to one-third of the length of the humerus plate, as measured from its proximal end. As will be noted, openings 20 are grouped into a consolidated arrangement 25. Such consolidation allows for the high plurality of fasteners into a tight grouping arrangement such that the grouped plurality of fasteners 20 creates a rafting arrangement upon penetration into the humerus bone. Importantly, a rafted arrangement of group 25 fasteners allows for a significant increase in support for the humerus head, as will be discussed.

In addition to the proximal openings 18 and the calcar openings 20, the proximal portion 12 of the humerus plate 10 can further include at least one drill guide opening 21 that can be used to secure another device, such as a drill guide, to the plate during the fixation procedure.

As shown, the central portion 14 includes a single elongated opening 22 and the distal portion 16 includes an additional openings 24. In some embodiments, the elongated opening 22 is approximately 3 to 6 mm wide and approximately 12 to 40 mm long. As indicated in FIG. 1, the opening 24 can comprise dual openings 26 that are joined together at their edges and that enable two independent fasteners to pass. In some embodiments, the openings 26 are each approximately 3 to 6 mm in diameter.

Figure 3:
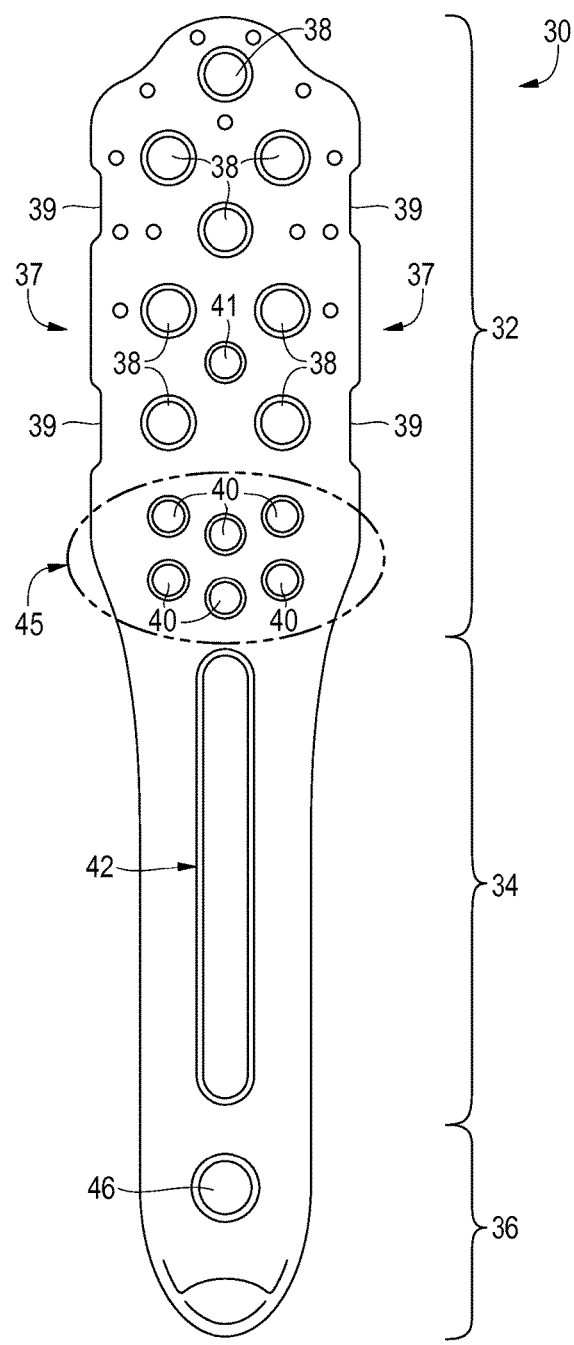
FIG. 3 is a front view of a second embodiment of a humerus plate that can be used to fix a proximal humerus fracture.

FIG. 3 illustrates a second embodiment of an implantable humerus plate 30 that can be used to secure bone fragments of the proximal humerus together. As is apparent from this figure, the humerus plate 30 is very similar to the humerus plate 10 shown in FIG. 1. Accordingly, the humerus plate 30 can be unitarily formed from a single piece of generally flat material and can generally comprise a proximal portion 32, a central portion 34, and a distal portion 36. The proximal portion 32 can have a gentle curvature that is adapted to match the curvature of the head of the humerus bone. As with the humerus plate 10, the humerus plate 30 can be approximately 80 to 100 mm long and approximately 2 to 5 mm thick.

The proximal portion 32 of the humerus plate 30 is wider than the central and distal portions 34, 36 of the plate. In some embodiments, the proximal portion 32 is approximately 18 to 20 mm wide and the central and distal portions 34, 36 are approximately 10 to 14 mm wide. As is further shown in FIG. 3, the proximal portion 32 can have a generally rectangular shape that is defined in part by generally linear edges 37. In some embodiments, the lateral edges 37 include notches 39 that may facilitate the attachment of another device to the humerus plate during the fixation procedure.

With further reference to FIG. 3, each of the portions 32-36 of the humerus plate 30 comprises its own opening or openings. As before, the proximal portion 32 can comprise relatively large proximal openings 38 (~3 to 5 mm in diameter) and relatively small calcar openings 40 (~2 to 3 mm in diameter). As in the previous embodiment, there are eight relatively large openings 38 that are generally equidistantly spaced from each other and six relatively small openings 40 that are arranged to two generally parallel rows of three openings each, although greater or fewer numbers of openings and different positioning of the openings can be used. In addition to the proximal openings 38 and the calcar openings 40, the proximal portion 32 of the humerus plate 30 can further include at least one drill guide opening 41 that can be used to secure another device to the plate during the fixation procedure.

Like the central portion 14 of the humerus plate 10, the central portion 34 includes a single elongated opening 42. However, the distal portion 36 of the humerus plate 30 includes a circular opening 46. In some embodiments, the elongated opening 42 is approximately 3 to 6 mm wide and approximately 12 to 40 mm long and the circular opening 46 is approximately 3 to 6 mm in diameter.

Figure 4:
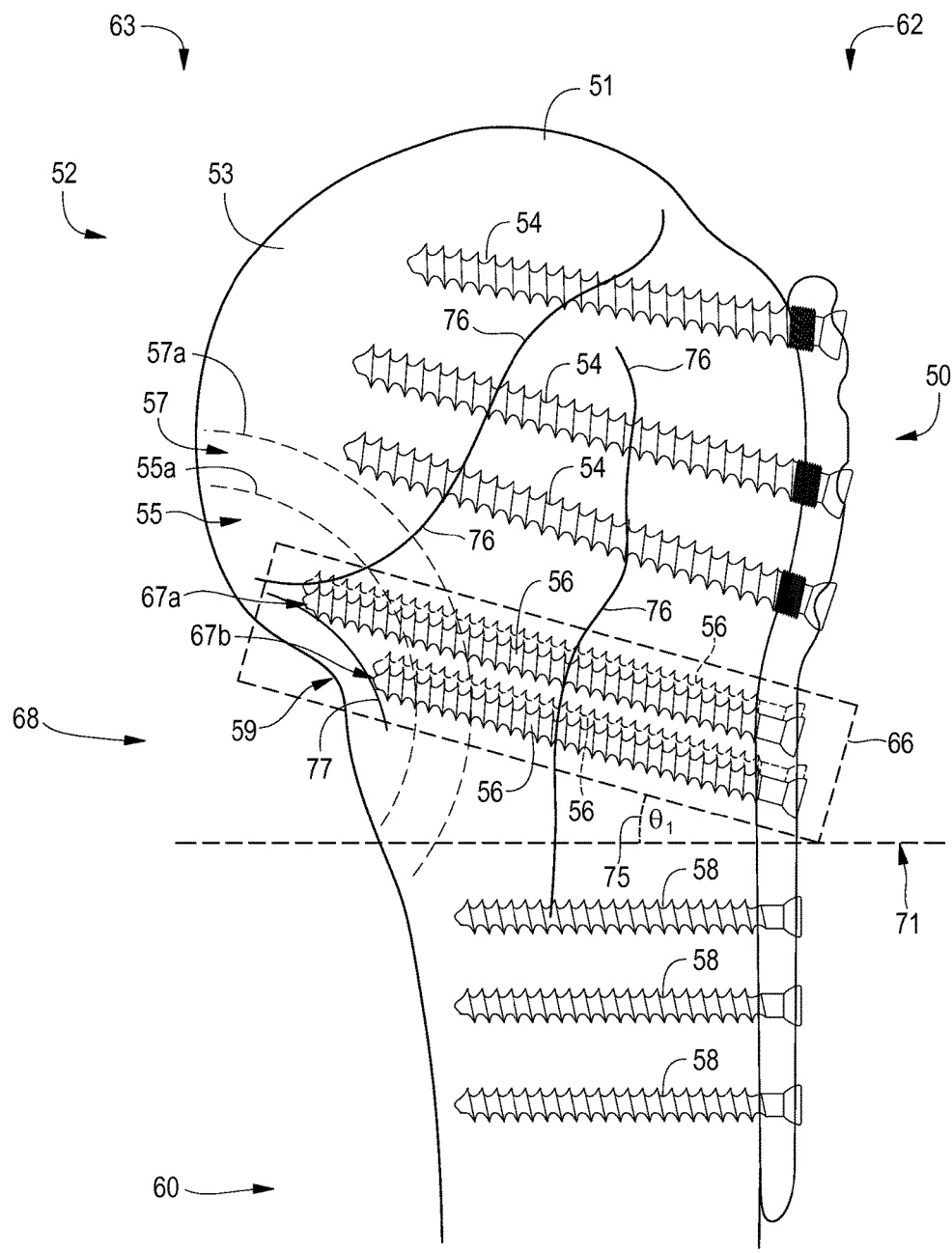
FIG. 4 is a side view of a humerus bone after the humerus plate of FIG. 3 has been affixed to the bone using bone screws.

With reference to FIG. 4, humerus plates of the type described above can be attached to the humeral head, neck, and shaft to fix the bone fragments together and ensure proper healing. In particular, the humerus plate 50 can be applied to the lateral side 62 of the humerus bone 52 and fasteners can be passed through the openings in the plate and into the bone 52 to secure the plate in place, so as to stabilize the bone fragments. In most embodiments, the humerus plate 50 is secured using bone screws as shown in FIG. 4.

The humerus plate 50 has a similar construction to the embodiment described in FIGS. 1-3, and is shown attached to the lateral side 62 of the head, neck, and shaft of a humerus bone 52 with multiple screws. In particular, relatively large proximal screws 54 have been passed through the proximal openings and into the humeral head 53, relatively small calcar screws 56 have been passed through the calcar openings and into the medial calcar region of the humerus 52, and relatively large central and distal screws 58 have been passed through the central and distal openings and into the shaft 60 of the humerus. Because of the multiple calcar screws 56 inserted into the medial calcar, greater structural integrity is provided to the calcar and the likelihood of varus collapse is greatly reduced.

As shown, the proximal screws 54 and the calcar screws 56 can be inserted into the humerus 52 at an angle. Preferably, the proximal screws 54 form an angle of approximately 20 to 30 degrees relative to a horizontal aspect line 71 (angle not shown) when the patient is in an upright orientation, and the calcar screws 56 form an angle $\theta_1$ (75) of approximately 20-25 degrees relative to a horizontal aspect line 71 (again when the patient is in an upright orientation). In some embodiments, the openings of the humerus plate 50 are configured so that the screws 54-58 can only pass through the plate at a predetermined angle. The screws 54-58 can either be solid screws or cannulated screws that have an internal passage that enables them to be passed over a guide, such as a metal pin. In some embodiments, the proximal, central, and distal screws 54, 58 each have a diameter of approximately 3 to 5 mm and the calcar screws 56 each have a diameter of approximately 2 to 3 mm. It is noted that, while bone screws are illustrated in FIG. 4, other fasteners, such as pegs or pins, may be used instead. Utilizing the above exemplary configuration of FIG. 4, the structure of the herein claimed fixation device for preventing a varus collapse shall now be described. It shall be noted that the calcar region of the humerus includes a primary calcar region 55 having an outer arcuate periphery 55a and an arcuate peripheral margin area 57 also have an outer boundary 57a. The primary calcar region 55 includes a lateral concave area 59 defined between the medial point of the anatomical neck and the medial point of the surgical neck of the humerus head 53, within the neck 68 of the humerus. The main calcar region 55 and in particular concave area 59 form a pressure region of the humerus neck 68 subject to disintegration upon the application of movement pressure of the humerus when compromised by a humerus head fracture. Normally, the medial aspect of the humeral neck and shaft 60 provide columnated support to the head 53 via calcar region 55, but fracture lines 76 compromise the ability of the head 53 to distribute torsional loads created by actuation of the strong rotator cuff muscles in the shoulder toward the lateral side 62 of humerus 52. Hence, rotation energy placed upon the humerus becomes concentrated toward the medial columnated support which overwhelms the calcar region 55 causing collapse. While screws 54 of fixation plate 50 assist in drawing head fragments along fracture lines 76 together in the fracture, the distribution effect of the osteo synthesis of the fragments is insufficient to distribute the axial compression and shear forces along the lateral region of the humerus 52. As force is applied between the head 53 and shaft 60 torsional forces exert pressure into and through calcar region 55, typically causing separation of outer periphery portion 57 from periphery 55a. This leads to displacement and angulation of bone fragments in the humeral head with resultant inversion movement of concave area 59 medially and downward, further reducing support to the head 53. Varus collapse occurs immediately thereafter.

Figure 6:
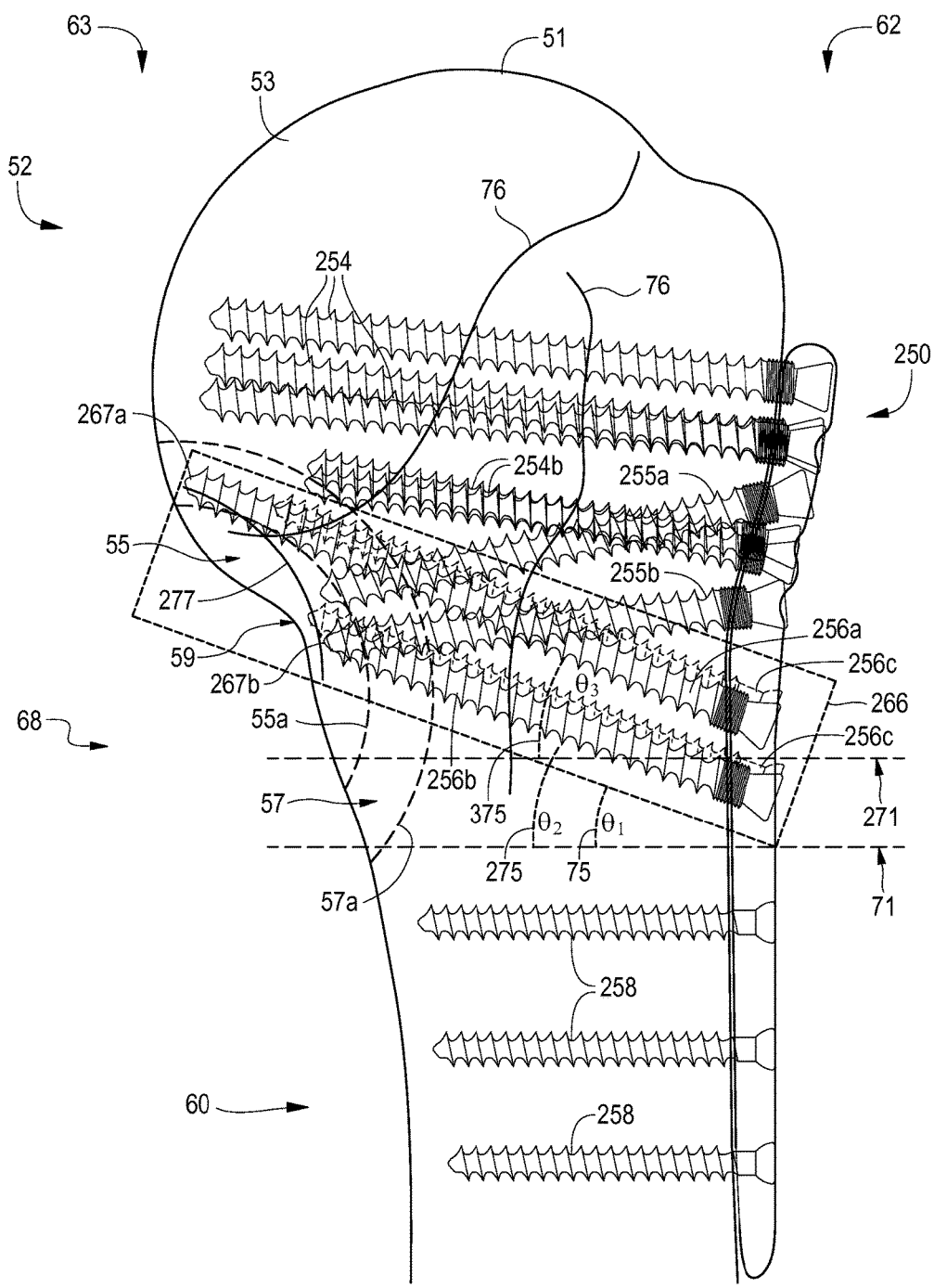
FIG. 6 is the plate of FIG. 5 shown in a side view affixed to the bone using bone screws having a novel cross-angled configuration.

However, such torsional forces within the calcar regions 55 can be substitutionally distributed by the novel arrangement shown in FIG. 4 (and FIG. 6). Specifically, plate 50 arranges a group (e.g. groups 25 and 45 of FIGS. 1 and 3) of calcar screws 56 into a rafted configuration 66 having parallel orientations with one another and extending along the humeral surgical neck and inferior portion of the humeral head. Critically, calcar screw tips 67 must penetration into the main calcar region 55 such that the upper calcar screw tips 67a penetrate above concave area 59 and the lower calcar screw tips 67b extend into a portion of the humeral neck adjacent to area 59. As shown, the screw tips 67 define an arc 77 matching the arc of the concave area 59 and penetrate within the cortical area of calcar region 55. Further, the calcar apertures (20 in area 25, and 40 in area 45—see FIGS. 1 and 3) are oriented into two parallel crescent shaped rows which causes screw tips 67a,b to also form a crescent shape together and which, therefore, follows the natural crescent shaped exterior of the calcar region 55 as it transitions upward into the humeral head 53. The aforementioned orientation of calcar screw penetration is achieved by forming plate 50 to orient calcar screw apertures (e.g. 20 and 40) having satisfactory angles to accomplish the aforementioned penetration configuration. The apertures 20, 40 confine the calcar screws to be oriented parallel to one another and upwardly angled by approximately 20-25 degrees 75 relative to a horizontal aspect line 71 (or 110-115 degrees relative to a vertical axis which is not shown), the angle 75 varying by approximately 5 degrees in relation to the patient's neck 68 and head 53 relative positions to achieve the above. The arrangement of the plate 50, apertures 20, 40, and fasteners 56, causes increased support to the calcar region 55 thereby stabilizing the inferior portion of head 53, and greatly increasing overall fracture fixation strength.

Figure 5:
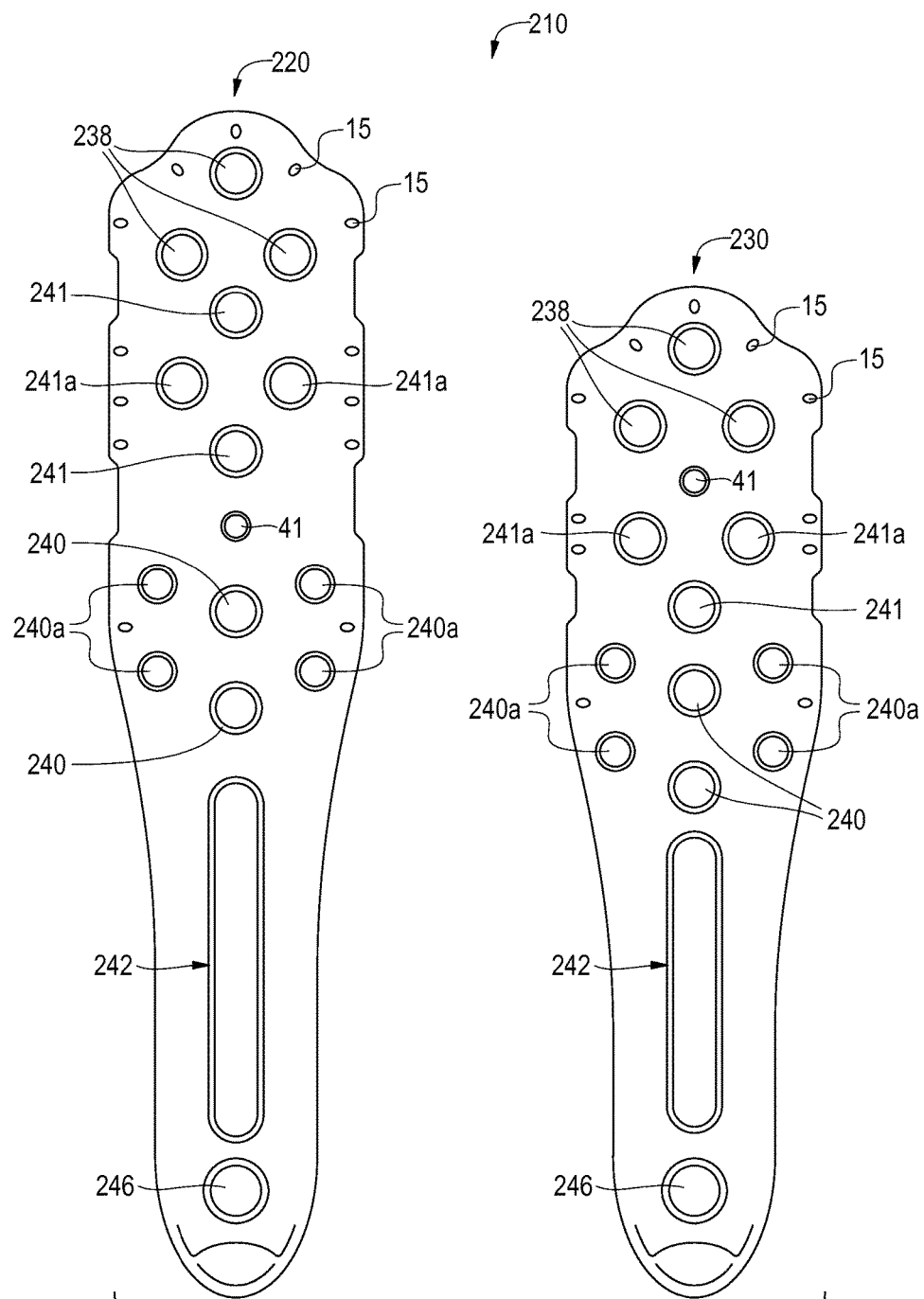
FIG. 5 is yet another configuration of the humerus plate having two sizes.

FIGS. 5 and 6 show an additional embodiment having a more complicated arraignment of fixation screws to further enhance the fixation plate's ability to prevent varus collapse. Pursuant to FIG. 5, the embodiment 210 has two size plates of 95 mm (220) and 80 mm (230) that will address most human humerus sizes. The plate 210 includes proximal openings 238 and two angled openings 241 aligned vertically. The smaller size 230 has only one angled opening 241 at the proximal end. Between the two openings 241 are two horizontally aligned openings 241a that are potentially smaller than the other openings 241. Below the openings 241 and 241a are 6 openings 240 to receive calcar screws. These openings 240(a) may be sized differently from the vertically aligned openings 240 and may be arranged to support varied angles of screw insertions. Both sizes of embodiment 210 have a slot 242 and a lower opening 246 as in the prior embodiments.

Referring to FIG. 6 and the larger form 220 of embodiment 210, the same humerus structures are shown as in FIG. 4 with the same goal to penetrate the calcar region 55 in order to prevent varus collapse as described above for FIG. 4. However, the screw arrangement for the embodiment shown in FIG. 6 is different. Proximal screws 254 pass through openings 238 into the humeral head 53 as in the embodiment in FIG. 4, however screws 255a and 255b pass through openings 241 and slant downward penetrating into calcar region 55 from above. Preferably, screws 255a and 255b angle towards each other slightly so that their tips will both penetrate into calcar region 55 at or above the concave area 59 while compressing the humeral head from slightly different angles. Smaller screws 254b pass through openings 241a and are angled slightly upwards to penetrate into humeral head 53 providing a cross compressive force with screws 255a,b.

Calcar screws 256a,b pass through openings 240 and extend across humerus 52 to penetrate into calcar region 55. Two pairs of smaller calcar screws 256c pass through openings 240a with each pair oriented to be parallel to one of the larger calcar screws 256a,b. Screws 256a,b and screws 256c together created a rafted configuration 266 of support screws similar to the rafted grouping 66 shown in FIG. 4, and also having an angle $\theta_1$ of between 20-25 degrees (75) relative to a horizontal reference line 71 as in FIG. 4. However, it will be noted that the angles of each calcar screw 256a and 256b, along with their parallel smaller pair of screws 256c, are slightly divergent relative to one another by 1-5 degrees. By allowing a small variation in angle between them, a greater optimal penetration of the tips 267a, 267b of screws 256a,b into the calcar region 55 can be achieved. In particular, by varying the angle slightly the screw tip placement 267a,b may be adjusted so that these tips penetrate beyond the calcar periphery 55a and into the calcar 55 region and, if desired, into the cortical margin of the calcar region 55. For example, angle $\theta_2$ (275) may have an angle of 20 degrees relative to horizontal reference line 71 and angle $\theta_3$ (375) may have angle of up to 25 degrees relative to horizontal reference line 271. This allows for utilization of a rafted screw configuration having superior column support within the humerus while allowing the raft to accommodate variable human anatomy. It will be noted that the tips of at least 4 affixation screws penetrate into the calcar region 55 with the configuration shown in FIG. 6. Hence, a better osteo synthesis may be achieved via the embodiment shown in FIG. 6.

The remainder of this specification pertains to methods and apparatus disclosed in PCT Application Serial No. PCT/US2014/011113, now published as of 17 Jul. 2014 under Publication No. WO2014/110421, herein incorporated by reference. While not referencing figures in the present application, the remainder specification information is provided as background support information for completeness of the subject matter claimed herein. References are made to the figures provided in the above stated PCT Application No. PCT/US2014/011113.

In some embodiments, fixation of the bone fragments can be achieved by compressing the bone fragments together before inserting all of the fasteners. FIGS. 5 and 6 illustrate an example apparatus suited for this purpose. More particularly, these figures show a compression device 60 that can be used to press the bone fragments together. As indicated FIG. 5, the compression device 60 includes two members 62 and 64 that are connected to each other at a central location along their lengths to form a hinge 65. The proximal portions of the members 62, 64 form grip handles 66, 68 that can be squeezed together by a surgeon or other user. The device 60 includes a spring element 70 that provides resistance to such squeezing and a locking ratchet mechanism 72 that locks the position of the handles 66, 68 when they are released. As the handles 66, 68 are squeezed together, the distance between distal ends 74 and 76 of the members 62, 64 is decreased. As indicated in FIGS. 5 and 6, pins 78 and 80 extend through the distal ends 74, 76 of the members 62, 64. These pins 78, 80 can be driven into the humerus bone using an appropriate driving device, such as a wire driver.

During a fixation procedure, the humerus plate can be attached to the humerus bone using one or more fasteners. In some embodiments, the fastener or fasteners can be inserted through the humerus plate and into the bone using a drill guide (not shown) that attaches to the humerus plate. By way of example, the humerus plate can be attached to the shaft of the bone using one or more distal screws. Next, the compression device 60 can be positioned relative to the humerus plate so that one of the pins 78, 80 aligns with one of the openings of the plate (e.g., a calcar opening) and one fragment of the bone and the other of the pins aligns with another fragment of the bone that is exposed to the side of the plate. The pins 78, 80 can then be driven into the bone (one passing through the plate and one not). At this point, the grip handles 66, 68 can be squeezed to press the bone fragments together and then the remainder of the fasteners can be passed through the humerus plate and into the bone to secure the fragments while they are in the pressed together state. In this manner, the humerus plate can be affixed while the bone fragments are in an optimal relative position for healing purposes.

In some embodiments, further fasteners can be inserted directly into the head of the humerus to provide additional reinforcement. More particularly, medial fasteners that extend in an anterior-to-posterior direction can be inserted into the humeral head that are perpendicular to the lateral fasteners that pass through the humerus plate. In such cases, an aiming apparatus can be utilized to ensure that the medial fasteners do not intersect the lateral fasteners.

Figure 7:
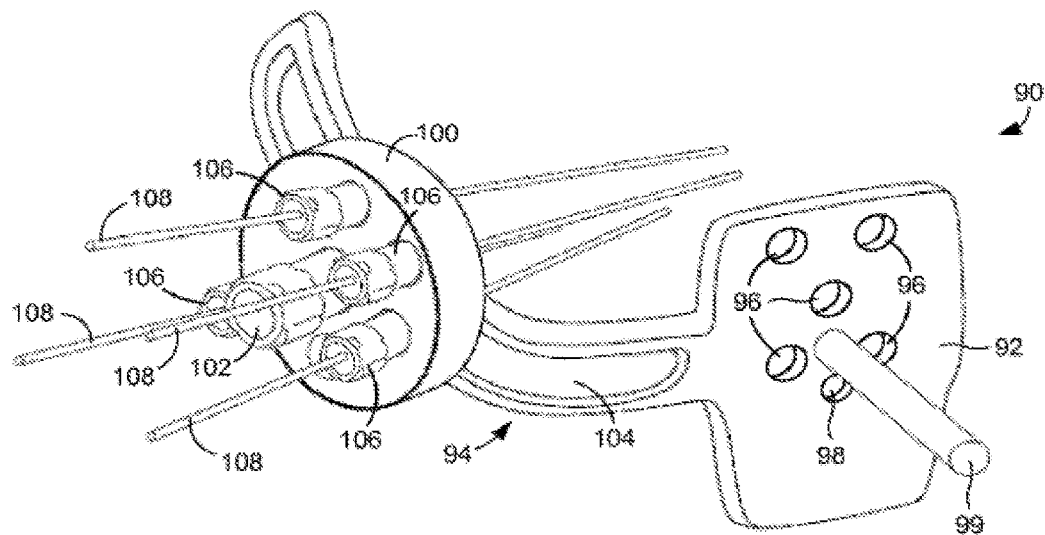
FIG. 7 is a perspective view of an embodiment of an aiming apparatus that can be used in a proximal humerus fixation procedure.

FIG. 7 shows an embodiment of an aiming apparatus 90 that can be used for the above-described purpose. As shown in this figure, the aiming apparatus 90 generally comprises a body 92 that is adapted to attach to the proximal portion of a humerus plate and an elongated arm 94 that extends laterally from the body and that curves to extend in a direction that is generally perpendicular to the plane in which the body resides. As shown in FIG. 7, the body 92 is configured as a generally flat rectangular plate that includes openings 96 that are adapted to align with the proximal openings of the proximal portion of the humerus plate. With such a configuration, the aiming apparatus 90 can be used as a guide for the fasteners that are to be passed through the proximal portion of the humerus plate and into the humeral head. In some embodiments, the body 92 further comprises tabs (not visible in FIG. 7) that are adapted to be received by the notches of the proximal portion of the humerus plate (see FIG. 1 or FIG. 3) so that the body 92 can snap-fit onto the proximal portion of the humerus plate (see FIG. 8). In addition, the body 92 can include a further opening 98 that is adapted to align with a drill guide opening provided in the proximal portion of the humerus plate to facilitate secure fastening of the aiming apparatus 90 to the humerus plate. Furthermore, the body 92 can include a handle 99 that can be used to grip and manipulate the body.

With further reference to FIG. 7, the aiming apparatus 90 also comprises a guide member 100 that is mounted to the arm 94. The guide member 100 secures to the arm 94 with a central fastener 102 that passes through an elongated slot 104 provided in the arm. When the fastener 102 is loose, the guide member 100 can be moved along the length of the arm 94. When the fastener 102 is tightened, however, the position of the guide member 100 along the arm 94 is fixed. With such a configuration, the guide member 100 can be moved along the length of the arm 94 either toward or away from the body 92 and, once the desired position has been reached, the fastener 102 can be tightened to fix the position of the guide member along the arm. The guide member 100 further comprises multiple guide elements 106 through which pins 108 can be passed. The orientations guide elements 106 are adjustable such that the orientations of the elements relative to the guide member 100 can be changed and fixed in desired orientations. Such adjustability enables the user to control the trajectory of each of the pins 108 so that the pins can be pressed into the head of the humerus with a desired trajectory (i.e., one in which they do not intersect the screws that extend through the humerus plate).

Figure 8:
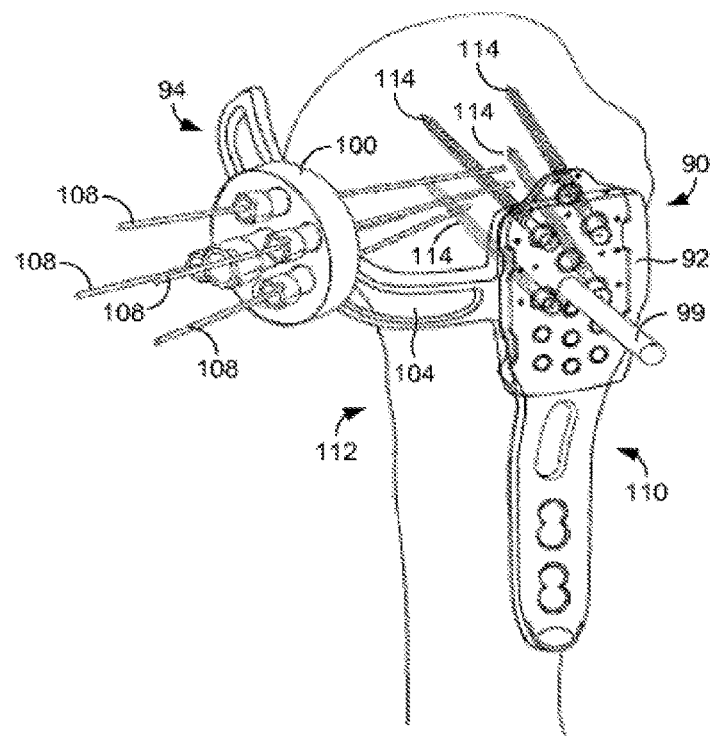
FIG. 8 is a perspective view of a humerus bone during an example proximal humerus fixation procedure.

FIG. 8 shows the aiming apparatus 90 attached to a humerus plate 110, which has been secured to a humerus bone 112 with multiple proximal screws 114. In such a situation, the aiming apparatus 90 can be used to ensure that the medial fasteners (e.g., screws) that will extend in an anterior-to-posterior direction within the humerus head will not intersect the proximal screws 114. To this end, the pins 108 can be passed through the guide elements 106 of the guide member 110 and into the bone 112. If one or more of the pins 108 intersects one or more of the screws 114, as determined by feel or fluoroscopic imaging, the pins can be removed, their trajectories can be changed, and they can be reinserted to see if they clear the screws. Once the pins 108 have been positioned within the bone 112 to the satisfaction of the surgeon, fasteners, such as cannulated screws, can be passed over the pins and the pins can be removed.

After the humerus plate has been secured to the bone, a locking mechanism can be used to prevent the fasteners from backing out of the bone and the plate. FIG. 9 illustrates an example locking plate 120 that can be used for this purpose. The plate 120 can comprise a plate of biocompatible material (e.g., stainless steel or titanium). As indicated in FIG. 10, the locking plate 120 can be sized and configured so as to cover the openings, and therefore fasteners, of the proximal portion of the humerus plate 122. In some embodiments, the locking plate 120 can be secured to the humerus plate 122 using a fastener (not shown) that passes through an opening 124 that aligns with the drill guide opening formed in the humerus plate.

Testing was performed to evaluate the benefits of calcar fixation in restoring medial stability. Eleven matched pairs of fresh-frozen cadaveric humeri were obtained from donors with a mean age of 69.5 years (range, fifty-four to eighty-one years) at the time of death and were stripped of all soft tissues. Dual energy x-ray absorptiometry (DXA) scans of each humerus were performed to provide a measure of bone mineral density within the humeral head. Prior to testing, each specimen was analyzed with fluoroscopy to ensure that there were no preexisting osseous defects. The proximal part of each humerus was osteotomized to create a standard three-part fracture involving the surgical neck and greater tuberosity. Five matched pairs were randomly assigned to have the medial calcar region remain intact and were designated as the non-comminuted group. The other six matched pairs had removal of a 10 mm medially based wedge of bone to simulate medial comminution or a fracture that lacks a medial buttress. These specimens were designated as the medial comminution group. Fracture fixation with use of a commonly used proximal humeral locking plate was performed by an orthopaedic surgeon according to the surgical technique guide. In order to optimize fixation, all of the fixation constructs had seven proximal locking screws placed in the subchondral bone. Within each pair of humeri, one shoulder was randomized to have calcar fixation (with use of two screws crossing the fracture into the humeral head) while the other did not have calcar fixation (with use of two short screws that did not cross the fracture). These were designated as the fixation and no-fixation specimens, respectively.

Mechanical testing was performed with use of a previously established method in which the distal humeral condyles were removed and the humeral shaft was potted in polymethylmethacrylate COE Tray Plastic (GC America, Chicago, Ill.) within an aluminum cylinder. This construct was then fixed in steel tubing that was welded to a base plate at 20° from vertical. Vertical compressive loads were applied to the superior aspect of the humeral head, 0.5 cm medial from the bicipital groove, with use of a 2 cm diameter cupped cylinder, producing axial and shear loading of the fixation. The constructs were loaded to failure at a rate of 10 cm/min with use of a uniaxial servo-hydraulic 858 Mini Bionix materials testing system (MTS Systems, Eden Prairie, Minn.). Actuator force and displacement were recorded with use of TestStar software (MTS Systems). Each trial was also recorded with a video camera to observe the onset and progression of the different modes of failure and to establish the point of failure on load-displacement curves.

The specimens with medial comminution were observed to angulate immediately upon application of the load with slippage along the medial fracture line, which was accompanied by pullout of the proximal screws. In these tests, the maximum load prior to closure of the medial cortical defect was considered as the load to failure. In contrast, the non-comminuted specimens were initially stiffer and resisted angulation on application of the load. As the loading increased, the medial fracture line expanded as a result of shearing and simultaneous angulation of the humeral head. In these tests, the load to failure was simply taken as the maximum load observed during the test.

After testing, the actuator load and displacement data were transferred to Excel software (Microsoft, Redmond, Wash.) to create load displacement curves. Values of load to failure, energy to failure, and displacement at the time of failure were determined from the load-displacement curves obtained for each construct. In addition, stiffness (defined as the slope of the linear portion of the load-displacement curve) was also determined for each specimen.

The effects of fracture type (comminuted or non-comminuted) and calcar fixation (fixation or no fixation) on the outcomes of load to failure, energy to failure, stiffness, and displacement to failure, while accounting for bone mineral density, were determined. A multivariate, random intercept regression model was fitted for each outcome with use of SAS software (version 9.13; SAS Institute, Cary, N.C.). This technique properly accounts for the paired nature of the specimens and quantifies the degree of correlation between pairs. Estimated means were derived from regression equations. Various models were explored with bone mineral density being considered as a linear or categorical variable, and all interactions (fracture type by calcar stability, fracture type by bone mineral density, calcar stability by bone mineral density) were examined. The results were analyzed with a significance level of p=0.05.

The medial comminution group without calcar fixation had the lowest values of load to failure, energy to failure, and stiffness. Each of these values increased, in ascending order, for the medial comminution group with calcar fixation, the no-comminution group without calcar fixation, and the non-comminution with calcar fixation (see Table I).

TABLE 1

Biomechanical Properties of the Four Constructs Tested*

| Outcome | Calcar Fixation | | | P Value | |
| --- | --- | --- | --- | --- | --- |
| | No | Yes | Overall | Fracture Type | Calcar Fixation |
| Load to failure (N) | | | | 0.015 | 0.002 |
| Comminuted | 463 | 682 | 564 | | |
| Noncomminuted | 985 | 1205 | 1087 | | |
| Overall | 716 | 935 | | | |
| Energy to failure (Nmm) | | | | 0.13 | 0.006 |
| Comminuted | 1976 | 3255 | 2554 | | |
| Noncomminuted | 3985 | 5264 | 4563 | | |
| Overall | 2919 | 4198 | | | |
| Stiffness (N/mm) | | | | 0.25 | 0.14 |
| Comminuted | 117 | 140 | 127 | | |
| Noncomminuted | 146 | 170 | 157 | | |
| Overall | 131 | 154 | | | |
| Displacement at failure (mm) | | | | 0.77 | 0.20 |
| Comminuted | 6.9 | 7.6 | 7.2 | | |
| Noncomminuted | 7.3 | 7.9 | 7.6 | | |
| Overall | 7.1 | 7.7 | | | |

*The estimated means and p values from the regression model are adjusted for bone mineral density.

Both calcar fixation and medial comminution had a significant effect on the load to failure. As detailed in Table I, specimens with medial comminution had a significantly lower mean load to failure as compared with non-comminuted specimens (p=0.015). The average load to failure in comminuted specimens decreased by 48% (523 N) when compared with non-comminuted specimens. Also, the use of appropriate calcar fixation screws resulted in 31% higher average load to failure (219 N) than in specimens without calcar fixation. This difference was significant (p=0.002).

The average bone mineral density values for the comminuted and non-comminuted groups were 0.50 and 0.65, respectively. Bone mineral density was not a significant predictor of any outcome measure, regardless of fracture type or the presence of calcar fixation. However, bone mineral density improved the overall multivariate regression model fit and was included in each regression model as a linear term. The final models included terms for fracture type, calcar stability, and bone mineral density but did not include interaction terms as interactions were not significant. In the regression analyses, the interaction effects were small compared with the main effects. Therefore, interactions again were not included, resulting in equal slopes among the regressions. The effect of bone mineral density was linear. The final models contained terms for fracture type, calcar stability, and bone mineral density, all without any interactions.

Similarly, the mean energy-to-failure value for the comminuted specimens was 2009 Nmm (44%) lower than that for the non-comminuted specimens. However, this decrease in load was not significant (p=0.13). In contrast, the average energy to failure for the constructs employing calcar fixation was 1279 Nmm (44%) higher than the average value for the constructs without calcar fixation (p=0.006). Stiffness was calculated as the slope of the linear portion of the load-displacement curve from the point of initial contact until marked discontinuity was observed, indicating failure. Although mean stiffness was 19% lower with comminuted specimens compared with non-comminuted specimens and 18% higher with calcar fixation than without, these differences were not statistically significant (p>0.1 for both). An increasing trend in average stiffness was observed among the different test groups (Table I), with the comminuted specimens (without calcar fixation) having the lowest value and the non-comminuted specimens (with calcar fixation) having the highest. Similarly, regression analysis showed that neither medial comminution nor calcar fixation had a significant effect on displacement at the time of failure (p=0.77 and p=0.20 respectively). Mean displacement 5% lower with comminuted specimens compared with non-comminuted specimens and 8% higher with calcar fixation than without. However, these differences were not significant (p>0.2 for both).

In view of these test results, it can be appreciated that calcar fixation significantly improves the stability of repaired fractures and is recommended as a surgical option, regardless of the achievement of an anatomic reduction with cortical contact medially. The results demonstrate the biomechanical advantage of medial cortical contact and calcar fixation and they provide an explanation for the results that are seen clinically.

While I have shown my invention in one form, it will be obvious to those skilled in the art that it is not so limited but is susceptible of various changes and modifications without departing from the spirit thereof.

Having set forth the nature of the invention, what is claimed is:

1. A proximal humerus fracture fixation system, comprising:
   a. an implantable humerus plate having a proximal portion adapted to be positioned along the lateral portions of the head and medial calcar of a human humerus, wherein the proximal portion includes lateral sides having notches adapted to receive tabs of a guide device configured to attach to the humerus plate with a snap-fit, and a distal portion adapted to be positioned along a portion of the shaft of said human humerus, the distal portion including a first slot having a length of approximately 12 to 40 mm and a width of approximately 3 to 6 mm and dual openings joined together at their edges so as to define a cross-sectional shape in the form of two overlapping circles;
   b. said proximal portion defining a plurality of apertures adapted to be positioned over the exterior of a lateral portion of said humeral head, and wherein each one of said apertures receives a respective one of a plurality of fasteners extending therethrough, and wherein said each said fastener is adapted to penetrate a substantial portion of said humeral head to secure said fractures in said head;
   c. said proximal portion further defining a grouping of smaller apertures positioned below said humeral head apertures and adapted to be positioned over a lateral inferior portion of said humeral head, each one of said smaller apertures receiving a respective one of the plurality of fasteners sized smaller than said humeral head fasteners and adapted for penetrating the calcar region of said humerus, wherein each said smaller fasteners are adapted to position their tips into the cortical portion of said calcar proximal the medial concave portion of said calcar, said where said tips are adapted to be spaced from an exterior surface of said medial concave portion of said calcar such that said tips remain, within said humerus bone; and
   d. wherein said distal portion of said plate defines at least one additional aperture for receiving a respective fastener adapted to secure said distal portion to said humerus.

2. The fixation system as recited in claim 1, wherein said smaller apertures positioned below said humeral head apertures are configured such that said smaller fasteners are formed into a single set.

3. The fixation system as recited in claim 2, wherein each fastener in said single set of fasteners has a respective longitudinal axis, and the single set of fasteners are positioned so the longitudinal axes are parallel to one another.

4. The fixation system as recited in claim 3, wherein said set of fasteners comprises an upper set of fasteners and a lower set, and wherein said upper set is adapted to penetrate a calcar area above said medial concave portion of said calcar and said lower set is adapted to penetrate a calcar area below said medial concave portion of said calcar.

5. The fixation system as recited in claim 2, wherein said set of fasteners defines an angle of more than 20 degrees relative to a horizontal aspect line bisecting the humerus.

6. The fixation system as recited in claim 5, wherein said set of fasteners comprises an upper set of fasteners and a lower set, and wherein said upper set is adapted to penetrate a calcar area above said medial concave portion of said calcar and said lower set is adapted to penetrate a calcar area below said medial concave portion of said calcar.

7. The fixation system as recited in claim 6, wherein each fastener in said single set of fasteners has a respective longitudinal axis, and the single set of fasteners are positioned so the longitudinal axes are positioned parallel to one another.

8. The fixation system as recited in claim 7, wherein said smaller apertures positioned below said humeral head apertures are configured into two crescent shaped rows of apertures such that said tips of said smaller calcar fasteners are adapted to be positioned to follow the natural curvature of the exterior of said humeral neck as it transitions into the inferior surface of said humeral head.

9. The fixation system as recited in claim 8, wherein said calcar fasteners are screws.

10. The fixation system as recited in claim 8, wherein said distal portion of said plate defines an extended slot.

11. The fixation system as recited in claim 1, wherein said set of fasteners comprises an upper set of fasteners and a lower set, and wherein said upper set is adapted to penetrate a calcar area above said medial concave portion of said calcar and said lower set is adapted to penetrate a calcar area below said medial concave portion of said calcar.

12. The fixation system as recited in claim 11, wherein said smaller apertures positioned below said humeral head apertures are configured into two rows of apertures, and the rows are curved, such that said tips of said smaller calcar fasteners are adapted to be positioned to follow the natural curvature of the exterior of said humeral neck as it transitions into the inferior surface of said humeral head.

13. In a fractured human humerus having an upper portion with a head, neck, and shaft, a fixation system for preventing the comminution of the calcar region in said humerus after surgical repair of said fractured humerus, comprising:
   a. a fixation plate adapted for affixation to and conformance with the lateral exterior of said human humerus, said plate having an upper proximal portion, and a lower distal portion, wherein the proximal portion is adapted to be positioned at a head and medial calcar of the humerus and includes lateral sides having notches adapted to receive tabs of a guide device configured to attach to the humerus with a snap-fit, and wherein the distal portion is adapted to be positioned along a shaft of the humerus, the distal portion including a first slot having a length of approximately 12 to 40 mm and a width of approximately 3 to 6 mm and dual openings joined together at their edges so as to define a cross-sectional shape in the form of two overlapping circles;
   b. a plurality of fasteners extending through said proximal portion and adapted for securing said plate to said humeral head;
   c. a plurality of fasteners positioned below said humeral head fasteners adapted for affixing said plate to the lateral exterior of said humerus and extending through the surgical neck and inferior portion of said humeral head of said humerus and into the calcar region of said humerus, said plurality of calcar fasteners comprising a grouping of fasteners wherein said tips of said fasteners are adapted to be positioned in the cortical margin of said calcar;
   d. wherein a portion of said plurality of fasteners that penetrate into said calcar region are configured to converge toward one another such that at least 4 fasteners have tips that penetrate simultaneously into said calcar region; and,
   e. said distal portion of said plate defining a slot having at least one fastener extending therethrough and adapted for securing said distal portion to said humeral shaft.

14. The fixation system as recited in claim 13, wherein said converging calcar fasteners are adapted to intersect one another and have each of their tips are positioned to penetrate into said calcar region, and wherein each said converging fasteners are sized and oriented such that the tips of said calcar fasteners are adapted to be positioned to follow the natural curvature of the exterior of said humeral neck as it transitions into the inferior surface of said humeral head.

15. The fixation system as recited in claim 14, wherein said set of calcar fasteners defines an angle of between 20 and 25 degrees relative to a horizontal aspect line bisecting the humerus, and at least one of said set of calcar fasteners has an angle of between 1 and 5 degrees difference relative to at least one other calcar fastener in said set and a horizontal aspect line bisecting the humerus.

16. A method of bone fixation in a fractured humerus, comprising:
   a. providing a fixation plate adapted to be affixed to said fractured humerus, said fixation plate comprising an upper proximal portion and a lower distal portion, two groups of apertures positioned in said proximal portion of said plate, one group positioned above the other, and at least one aperture positioned in said lower distal portion of said plate, wherein the proximal portion is adapted to be positioned at a head and medial calcar of the humerus, wherein the proximal portion includes lateral sides having notches adapted to receive tabs of a guide device configured to attach to the humerus plate with a snap-fit, and the distal portion is adapted to be positioned along a shaft of the humerus, the distal portion including a first slot having a length of approximately 12 to 40 mm and a width of approximately 3 to 6 mm and dual openings joined together at their edges so as to define a cross-sectional shape in the form of two overlapping circles, said fixation plate comprising;
   b. securing said plate to the head of said humerus with a plurality of fasteners, each of the plurality of fasteners extending through said proximal portion at a respective one of the upper group of apertures and into said humeral head;
   c. securing said plate to the neck of said humerus by extending each one of a plurality of fasteners through a respective one of said lower group of apertures in the proximal portion of said plate, such that respective longitudinal axes of the fasteners are parallel, and extending the tips of said fasteners through the surgical neck and inferior portion of said humeral head of said humerus and into the calcar region of said humerus; and,
   d. wherein said step of securing said plate to the neck of said humerus further includes the steps of positioning the fastener set to form an angle of between 20 and 25 degrees from a horizontal aspect line; and,
   e. securing the distal portion of said plate to the shaft of said humerus.

17. The method as recited in claim 16, further including the step of positioning the tips of said fasteners into the cortical margin of said calcar region such that they define an arc equally spaced from the concave exterior surface of said calcar region.

18. The method as recited in claim 17, further including the step of orienting and sizing the fasteners in the lower aperture group of the proximal portion of said plate such that the tips of said calcar fasteners follow the contours of the exterior of said calcar region.

19. The method as recited in claim 17, further including the step of drawing the different portions of any fractures in said humeral head together prior to affixing said plate to said lateral side of said humerus such that said plate and fasteners form an osteo synthesis that resists calcar collapse.

20. The method as recited in claim 17, further including the step of positioning at least two fasteners to intersect one another with both penetrating into the calcar region, and wherein at least two calcar fasteners are convergently positioned and angled to be within 5 degrees of to one another.

* * * * *